US008728504B2

(12) United States Patent
Bruchmann et al.

(10) Patent No.: US 8,728,504 B2
(45) Date of Patent: May 20, 2014

(54) PROCESS FOR SOLUBILIZING HYDROPHOBIC ACTIVE INGREDIENTS IN AQUEOUS MEDIUM

(75) Inventors: Bernd Bruchmann, Freinsheim (DE); Holger Türk, Mannheim (DE); Daniel Schönfelder, Brussels (BE); Monika Haberecht, Ludwigshafen (DE); Dietmar Appelhans, Dresden (DE); Victor Boyko, St. Petersbur (RU)

(73) Assignee: BASF SE, Ludwigshafen (DE)

(*) Notice: Subject to any disclaimer, the term of this patent is extended or adjusted under 35 U.S.C. 154(b) by 327 days.

(21) Appl. No.: 13/021,190

(22) Filed: Feb. 4, 2011

(65) Prior Publication Data

US 2011/0195844 A1    Aug. 11, 2011

Related U.S. Application Data

(60) Provisional application No. 61/301,634, filed on Feb. 5, 2010.

(51) Int. Cl.
| | |
|---|---|
| *A01N 25/00* | (2006.01) |
| *A01N 33/02* | (2006.01) |
| *A01N 47/28* | (2006.01) |
| *A01N 43/04* | (2006.01) |
| *A61K 9/14* | (2006.01) |
| *A61K 47/30* | (2006.01) |
| *A61K 31/13* | (2006.01) |
| *A61K 31/17* | (2006.01) |
| *A61K 31/70* | (2006.01) |
| *A61K 31/715* | (2006.01) |
| *C07C 273/00* | (2006.01) |
| *C07H 1/00* | (2006.01) |
| *C13K 5/00* | (2006.01) |

(52) U.S. Cl.
USPC ........... 424/405; 424/406; 424/488; 504/327; 514/23; 514/53; 514/54; 514/588; 514/663; 514/673; 514/772.3; 536/123.1; 536/123.13; 564/32; 564/63; 564/511

(58) Field of Classification Search
USPC .............. 525/438, 167.5, 174, 187, 425, 440, 525/442–448, 457; 528/60, 220, 272, 295, 528/298, 302, 308, 370, 373, 39; 424/405, 424/409, 493, 499, 78.17, 78.37; 514/2.3, 514/3.3, 4.5, 21.9, 772.1, 773
See application file for complete search history.

(56) References Cited

U.S. PATENT DOCUMENTS

| | | | |
|---|---|---|---|
| 2009/0041813 A1* | 2/2009 | Bouillo et al. | ................. 424/401 |
| 2009/0099319 A1 | 4/2009 | Stumbe et al. | |
| 2012/0238641 A1 | 9/2012 | Türk et al. | |
| 2012/0309626 A1 | 12/2012 | Türk et al. | |
| 2012/0309629 A1 | 12/2012 | Türk et al. | |

FOREIGN PATENT DOCUMENTS

| | | |
|---|---|---|
| DE | 33 16 510 A1 | 11/1984 |
| EP | 0 462 456 A1 | 12/1991 |
| EP | 0 560 138 A1 | 9/1993 |
| EP | 0 897 904 A1 | 2/1999 |
| WO | WO 98/46608 A1 | 10/1998 |
| WO | WO 99/41255 A1 | 8/1999 |
| WO | WO 03/004456 A2 | 1/2003 |
| WO | WO 03/004456 A3 | 1/2003 |
| WO | WO 03/066702 A1 | 8/2003 |
| WO | WO 03/075663 A1 | 9/2003 |
| WO | WO 2005/044897 A1 | 5/2005 |
| WO | WO 2005/075541 A1 | 8/2005 |
| WO | WO 2006/018125 A1 | 2/2006 |
| WO | WO 2006/087227 A2 | 8/2006 |
| WO | WO 2006/087227 A3 | 8/2006 |
| WO | WO 2007/060119 A1 | 5/2007 |
| WO | WO 2007/125028 A1 | 11/2007 |

OTHER PUBLICATIONS

Yoann M. Chabre et al., "Recent Trends in Glycodendrimer Syntheses and Applications," Jan. 2008, Current Topics in Medicinal Chemistry, 8(14):1237-1285.*
Huricha Baigude et al., "Synthesis of Sphere-Type Monodispersed Oligosaccharide-Polypeptide Dendrimers," Sep. 23, 2003; Macromolecules, 36(19):7100-7106.*
International Search Report issued Jun. 21, 2011, in Patent Application No. PCT/EP2011/051292 (with English Translation of Category of Cited Documents).
Yoann M. Chabre, et al., "Recent Trends in Glycodendrimer Syntheses and Applications", Current Topics in Medicinal Chemistry, vol. 8, No. 14, XP 2631711, Jan. 2008, pp. 1237-1285.
Cyrille Grandjean, et al., "Novel Hyperbranched Glycomimetics Rocognized by the Human Mannose Receptor: Quinic or Shikimic Acid Derivatives as Mannose Bioisosteres", Chembiochem, vol. 2, XP 2634620, Sep. 28, 2001, pp. 747-757.
Huricha Baigude, et al., "Synthesis of Sphere-Type Monodispersed Oligosaccharide-Polypeptide Dendrimers", Macromolecules, vol. 36, No. 19, XP 2634826, Sep. 23, 2003, pp. 7100-7106.
U.S. Appl. No. 13/028,624, filed Feb. 16, 2011, Roller et al.

* cited by examiner

*Primary Examiner* — Jane C Oswecki
(74) *Attorney, Agent, or Firm* — Oblon, Spivak, McClelland, Maier & Neustadt, L.L.P.

(57) ABSTRACT

A process for solubilizing hydrophobic active ingredients in aqueous medium, which comprises using, as an assistant, at least one hyperbranched polymer (A) which is obtainable by reacting at least one hyperbranched polymeric compound having at least one primary or secondary amino group per molecule (a), selected from
(a1) hyperbranched polyamides and
(a2) hyperbranched polyureas,
with
(b) at least one mono-, di- or oligosaccharide.

17 Claims, No Drawings

PROCESS FOR SOLUBILIZING HYDROPHOBIC ACTIVE INGREDIENTS IN AQUEOUS MEDIUM

The present invention relates to a process for solubilizing hydrophobic active ingredients in aqueous medium, which comprises using, as an assistant, at least one hyperbranched polymer (A) which is obtainable by reacting at least one hyperbranched polymeric compound having at least one primary or secondary amino group per molecule (a), selected from
(a1) hyperbranched polyamides and
(a2) hyperbranched polyureas,
with
(b) at least one mono-, di- or oligosaccharide.

The present invention further relates to hyperbranched polymers (A) which are obtainable by reacting at least one hyperbranched polymeric compound having at least one primary or secondary amino group per molecule (a), selected from
(a1) hyperbranched polyamides and
(a2) hyperbranched polyureas,
with
(b) at least one mono-, di- or oligosaccharide
in the liquid phase.

The present invention further relates to complexes comprising at least one inventive hyperbranched polymer and at least one hydrophobic active ingredient, and to a process for preparing inventive complexes. The present invention further relates to a process for preparing inventive hyperbranched polymers.

In many cases, it is necessary to solubilize hydrophobic substances, for example hydrophobic active ingredients, in water without chemically altering the active ingredient in question as such. For this purpose, it is possible, for example, to prepare an emulsion, in which case the active ingredient in question is present in the oil phase of the emulsion. For many active pharmaceutical ingredients or crop protection agents, especially for those which are to be transported with a body fluid or in a plant's sap, such an operation, however, is impossible. Emulsions can break under the action of high shear forces. Moreover, sterilization with retention of the emulsion is impossible in many cases.

It is known, for example, from DE-A 33 16 510 that hydrophobic active pharmaceutical ingredients can be dissolved in solvent mixtures of ethanol and water and propylene glycol or polyethylene glycol, and can be processed to give, for example, parenterally administrable formulations. Such solvent mixtures generally comprise 15 to 30% by weight of ethanol. However, it is desirable in many cases to avoid such large amounts of alcohol in the treatment of ill persons.

Additionally known is the solubilization of active ingredients based on 1,4-dihydropyridines with phospholipids, specifically liposome phospholipids, in water; see, for example, EP 0 560 138 A. Liposome phospholipids are, however, subject to the same degradation mechanisms as in endogenous cell membrane lipids. Liposomal transport systems produced in this way therefore only have a limited shelf life, according to the pH and ionic strength of the medium. Especially as a result of the shear forces which occur in the course of intravenous administration of the active ingredients, liposomal transport systems can easily be destroyed.

Furthermore, in many cases, excessively high concentrations of the solubilizing agent and of the active ingredient in the liver or in the spleen are observed as undesired transport from the blood vessels into the surrounding tissue, and slow release of the encapsulated active ingredient is observed even after a short time owing to the dynamic structure of the lipid double layer. The difficulty of sterilization is a further reason why liposomes are not suitable for all applications in active ingredient transport.

Further systems for solubilizing hydrophobic active ingredients are known, for example, from WO 2007/125028.

WO 2007/060119 discloses hyperbranched polylysines, and the use thereof as solubilizers is proposed. However, the properties thereof in the solubilization of hydrophobic substances are insufficient for many purposes and can be improved further.

WO 2006018125 discloses highly branched polyamides and the use thereof for producing moldings, films, fibers and foams.

WO 2006/087227 discloses combinations of at least one hydrophobic active ingredient and hyperbranched nitrogen-containing polymers, for example polyureas. However, the properties thereof in the solubilization of hydrophobic substances are insufficient for many purposes and can be improved further.

D. Appelhans et al, *Biomacromolecules* 2009, 10, 1114 and D. Appelhans et al., *Molecular Bioscience* 2007, 7, 373 disclose that hyperbranched polyethyleneimines joined to oligosaccharides can be used to complex pharmaceutical substances.

A disadvantage of the known systems for solubilizing hydrophobic active ingredients in aqueous media is that they can solubilize only small amounts of active ingredient. Moreover, many of the unfunctionalized hyperbranched polymers used, for example many polyamides and polyureas, are often not water-soluble or not water-dispersible per se, such that they are unsuitable for solubilization in aqueous media. Furthermore, polyethyleneimine-containing solubilizers have the disadvantage that, owing to the amino groups still present in large numbers even after the functionalization, they have excessively polar structures which are not suitable for solubilizing hydrophobic active ingredients.

It was thus an object of the present invention to provide an improved process for solubilizing hydrophobic active ingredients which does not have the disadvantages known from the prior art. It was a further object of the present invention to provide transport systems which avoid the disadvantages known from the prior art.

Accordingly, the process defined at the outset has been found.

Solubilization is understood to mean that active ingredient which is hydrophobic in an aqueous medium, in other words insoluble or sparingly soluble per se, can be distributed in molecular dispersion. This can be done, for example, by complexing or enveloping the relevant hydrophobic active ingredient.

In the context of the present invention, an aqueous medium is understood to mean, for example, the following: water, solvent mixtures of water and at least one organic solvent, for example methanol, ethanol, ethylene glycol, propylene glycol, polyethylene glycol, isopropanol, 1,4-dioxane or N,N-dimethylformamide, aqueous sugar solutions, for example aqueous glucose solution, aqueous salt solutions, for example aqueous sodium chloride solutions or aqueous potassium chloride solutions, aqueous buffer solutions, for example phosphate buffer, or, especially, plant saps or human or animal body fluids containing water, for example blood, urine, and splenic fluid.

Preferably, an aqueous medium is understood to mean pure (distilled) water, aqueous sodium chloride solution, especially physiological saline solution, or solvent mixtures of water with at least one of the abovementioned organic solvents, the proportion of organic solvent not exceeding 10% by weight of the aqueous medium in question.

Active ingredients in the context of the present invention can also be termed effect substances and are substances of the kind which have, for example, an action as a crop protection agent, for example as an insecticide, herbicide or fungicide, preferably as an insecticide and fungicide, or which are effective as a fluorescent agent or have pharmaceutical action, for example as a cardiovascular agent or against osteoporosis or as a cytostatic. Pigments are not active ingredients in the context of the present invention.

Examples of suitable cardiovascular agents are, for example, those of the formula I.

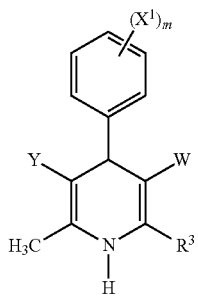

I

In this formula the variables and radicals are defined as follows:

Y is $NO_2$, CN or $COOR^1$, where
$R^1$ is $C_1$-$C_4$ alkyl, such as methyl, ethyl, n-propyl, isopropyl, n-butyl, isobutyl, sec-butyl, tert-butyl, unsubstituted or substituted one or more times by $C_1$-$C_3$ alkoxy, such as methoxy, ethoxy, n-propoxy, isopropoxy; examples of substituted radicals $R^1$ are for example methoxymethyl, ethoxymethyl, 2-methoxyethyl.
W is CO—NH—$C_3$-$C_7$ cycloalkyl or $COOR^2$, where
$R^2$ is selected from $C_1$-$C_{10}$ alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl; with particular preference $C_1$-$C_4$ alkyl such as methyl, ethyl, n-propyl, isopropyl, n-butyl, isobutyl, sec-butyl, and tert-butyl, especially methyl unsubstituted or substituted one or more times by $C_1$-$C_3$ alkoxy, trifluoromethyl, N-methyl-N-benzylamino or $CH_2$—$C_6H_5$. Examples of substituted radicals $R^2$ are for example methoxymethyl, ethoxymethyl, 2-methoxyethyl, 2,2,2-trifluoroethyl.
$R^3$ is selected from CN, ω-hydroxyalkyl, preferably ω-hydroxy-$C_1$-$C_4$-alkyl, especially hydroxymethyl and 2-hydroxyethyl, or $C_1$-$C_4$ alkyl such as methyl, ethyl, n-propyl, isopropyl, n-butyl, isobutyl, sec-butyl and tert-butyl.
$X^1$ is in each case alike or different and selected from $NO_2$, halogen, especially fluorine, chlorine or bromine, $C_1$-$C_4$ alkyl such as methyl, ethyl, n-propyl, isopropyl, n-butyl, isobutyl, sec-butyl, and tert-butyl, $C_1$-$C_4$ alkoxy, such as methoxy, ethoxy, n-propoxy, isopropoxy, n-butoxy, isobutoxy, sec-butoxy, tert-butoxy; benzoyl, acetyl, O—CO—$CH_3$, trifluoromethyl or 2-(4-methylbenzyloxy).
m is selected from whole numbers in the range from zero to two, preferably one or two.

Examples of particularly suitable active pharmaceutical ingredients include nifedipine, nimodipine (1,4-dihydro-2,6-dimethyl-4-(3'-nitrophenyl)pyridine 3-β-methoxyethyl ester 5-isopropyl ester, known from DE 28 15 278), nisoldipine, nitrendipine, felodipine, and amlodipine.

In connection with active ingredients, hydrophobic is understood to mean that the solubility in distilled water at 20° C. is preferably below 1 g/l, more preferably below 0.1 g/l.

Examples of suitable cytostatics are doxorubicin and paclitaxel.

Further suitable active pharmaceutical ingredients are those which are active against osteoporosis, inflammation or rheumatism.

Further suitable active pharmaceutical ingredients in the context of the present invention are hormones, proton pump inhibitors, statins, proteasome inhibitors, analgesics and cholesterol-lowering agents.

Examples of suitable active fungicidal ingredients which can be solubilized in accordance with the process of the invention comprise the following:

acylalanines such as benalaxyl, metalaxyl, ofurace, oxadixyl;

amine derivatives such as aldimorph, dodine, dodemorph, fenpropimorph, fenpropidin, guazatine, iminoctadine, spiroxamin, tridemorph;

anilinopyrimidines such as pyrimethanil, mepanipyrim or cyrodinyl;

antibiotics such as cycloheximide, griseofulvin, kasugamycin, natamycin, polyoxin, and streptomycin;

azoles such as bitertanol, bromoconazole, cyproconazole, difenoconazole, dinitroconazole, epoxiconazole, fenbuconazole, fluquiconazole, flusilazole, flutriafol, hexaconazole, imazalil, ipconazole, metconazole, myclobutanil, penconazole, propiconazole, prochloraz, prothioconazole, tebuconazole, tetraconazole, triadimefon, triadimenol, triflumizole, triticonazole;

2-methoxybenzophenones, as described by the general formula I in EP 0 897 904, e.g., metrafenone;

dicarboximides such as iprodione, myclozolin, procymidone, vinclozolin;

dithiocarbamates such as ferbam, nabam, maneb, mancozeb, metam, metiram, propineb, polycarbamate, thiram, ziram, zineb;

heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, picobezamid, probenazole, proquinazid, pyrifenox, pyroquilon, quinoxyfen, silthiofam; thiabendazole, thifluzamid, thiophanate-methyl, tiadinil, tricyclazole, triforine;

nitrophenyl derivatives such as binapacryl, dinocap, dinobuton, nitrophthal-isopropyl; phenylpyrroles such as fenpiclonil and also fludioxonil;

unclassified fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin acetate, fenoxanil, ferimzone, fluazinam, fosetyl, fosetyl aluminum, iprovalicarb, hexachlorobenzene, metrafenone, pencycuron, propamocarb, phthalide, toloclofos-methyl, quintozene, zoxamide;

strobilurins as described by the general formula I in WO 03/075663, examples being azoxystrobin, dimoxystrobin, fluoxastrobin, kresoxim-methyl, metominostrobin, orysastrobin, picoxystrobin, pyraciostrobin, and trifloxystrobin;

sulfenic acid derivatives such as captafol, captan, dichlofluanid, folpet, tolylfluanid;

cinnamamides and analogs such as dimethomorph, flumetover, flumorph;

6-aryl-[1,2,4]triazolo[1,5-a]pyrimidines as described by the general formula I in each for example of WO 98/46608, WO 99,41255 or WO 03/004465;

amide fungicides such as cyclofenamid and also (Z)—N-[α-(cyclopropylmethoxyimino)-2,3-difluoro-6-(difluoromethoxy)benzyl]-2-phenylacetamide.

Examples of herbicides comprise the following:

1,3,4-thiadiazoles such as buthidazole and cyprazole;

amides such as allidochlor, benzoylpropethyl, bromobutide, chlorthiamid, dimepiperate, dimethenamid, diphenamid, etobenzanid, flamprop-methyl, fosamin, isoxaben, metazachlor, monalide, naptalam, pronamide, propanil;

aminophosphoric acids such as bilanafos, buminafos, glufosinate ammonium, glyphosate, sulfosate;

aminotriazoles such as amitrole, anilides such as anilofos, mefenacet;

aryloxyalkanoic acid such as 2,4-D, 2,4-DB, clomeprop, dichlorprop, dichlorprop-P, dichlorprop-P, fenoprop, fluoroxypyr, MCPA, MCPB, mecoprop, mecoprop-P, napropamide, napropanilide, triclopyr;

benzoic acids such as chloramben, dicamba;

benzothiadiazinones such as bentazone;

bleachers such as clomazone, diflufenican, fluorochloridone, flupoxam, fluridone, pyrazolate, sulcotrione;

carbamates such as carbetamid, chlorbufam, chlorpropham, desmedipham, phenmedipham, vernolate;

quinolinic acids such as quinclorac, quinmerac;

dichloropropionic acids such as dalapon;

dihydrobenzofurans such as ethofumesate;

dihydrofuran-3-one such as flurtamone;

dinitroanilines such as benefin, butralin, dinitramin, ethalfluralin, fluchloralin, isopropalin, nitralin, oryzalin, pendimethalin, prodiamine, profluralin, trifluralin, dinitrophenols such as bromofenoxim, dinoseb, dinoseb acetate, dinoterb, DNOC, minoterb acetate;

diphenyl ethers such as acifluorfen sodium, aclonifen, bifenox, chlornitrofen, difenoxuron, ethoxyfen, fluorodifen, fluoroglycofen ethyl, fomesafen, furyloxyfen, lactofen, nitrofen, nitrofluorfen, oxyfluorfen;

dipyridyls such as cyperquat, difenzoquat methyl sulfate, diquat, paraquat dichloride;

imidazoles such as isocarbamid;

imidazolinones such as imazamethapyr, imazapyr, imazaquin, imazethabenz methyl, imazethapyr, imazapic, imazamox;

oxadiazoles such as methazole, oxadiargyl, oxadiazon;

oxiranes such as tridiphane;

phenols such as bromoxynil, ioxynil;

phenoxyphenoxypropionic esters such as clodinafop, cyhalofop butyl, diclofop methyl, fenoxaprop ethyl, fenoxaprop p-ethyl, fenthiaprop ethyl, fluazifop butyl, fluazifop p-butyl, haloxyfop ethoxyethyl, haloxyfop methyl, haloxyfop p-methyl, isoxapyrifop, propaquizafop, quizalofop ethyl, quizalofop p-ethyl, quizalofop tefuryl;

phenylacetic acids such as chlorfenac;

phenylpropionic acids such as chlorophenprop methyl;

ppi (ppi=preplant incorporated) active ingredients such as benzofenap, flumiclorac pentyl, flumioxazin, flumipropyn, flupropacil, pyrazoxyfen, sulfentrazone, thidiazimin;

pyrazoles such as nipyraclofen;

pyridazines such as chloridazon, maleic hydrazide, norflurazon, pyridate;

pyridinecarboxylic acids such as clopyralid, dithiopyr, picloram, thiazopyr;

pyrimidyl ethers such as pyrithiobac acid, pyrithiobac sodium, KIH-2023, KIH-6127;

sulfonamides such as flumetsulam, metosulam;

triazolecarboxamides such as triazofenamid;

uracils such as bromacil, lenacil, terbacil;

and additionally benazolin, benfuresate, bensulide, benzofluor, bentazone, butamifos, cafenstrole, chlorthal dimethyl, cinmethylin, dichlobenil, endothall, fluorbentranil, mefluidide, perfluidone, piperophos, topramezone, and prohexandione-calcium;

sulfonylureas such as amidosulfuron, azimsulfuron, bensulfuron methyl, chlorimuron ethyl, chlorsulfuron, cinosulfuron, cyclosulfamuron, ethametsulfuron methyl, flazasulfuron, halosulfuron methyl, imazosulfuron, metsulfuron methyl, nicosulfuron, primisulfuron, prosulfuron, pyrazosulfuron ethyl, rimsulfuron, sulfometuron methyl, thifensulfuron methyl, triasulfuron, tribenuron methyl, triflusulfuron methyl, tritosulfuron;

active crop protection ingredients of the cyclohexenone type such as alloxydim, clethodim, cloproxydim, cycloxydim, sethoxydim, and tralkoxydim.

Very particularly preferred active herbicidal ingredients of the cyclohexenone type are:

tepraloxydim (cf. AGROW, No. 243, Nov. 3, 1995, page 21, caloxydim), and 2-(1-[2-{4-chlorophenoxy}propyloxyimino]butyl)-3-hydroxy-5-(2H-tetrahydrothiopyran-3-yl)-2-cyclohexen-1-one and of the sulfonylurea type: N-(((4-methoxy-6-[trifluoromethyl]-1,3,5-triazin-2-yl)-amino)carbonyl)-2-(trifluoromethyl)benzenesulfonamide.

Examples of suitable insecticides comprise the following:

organophosphates such as acephate, azinphos-methyl, chlorpyrifos, chlorfenvinphos, diazinon, dichlorvos, dimethylvinphos, dioxabenzofos, dicrotophos, dimethoate, disulfoton, ethion, EPN, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, primiphos-ethyl, pyraclofos, pyridaphenthion, sulprophos, triazophos, trichlorfon; tetrachlorvinphos, vamidothion carbamates such as atanycarb, benfuracarb, bendiocarb, carbaryl, carbofuran, carbosulfan, fenoxycarb, furathiocarb, indoxacarb, methiocarb, methomyl, oxamyl, pirimicarb, propoxur, thiodicarb, triazamate;

pyrethroids such as bifenthrin, cyfluthrin, cycloprothrin, cypermethrin, deltamethrin, esfenvalerate, ethofenprox, fenpropathrin, fenvalerate, cyhalothrin, lambda-cyhalo-thrin, permethrin, silafluofen, tau-fluvalinate, tefluthrin, tralomethrin, alpha-cypermethrin, zeta-cypermethrin, permethrin;

arthropodal growth regulators: a) chitin synthesis inhibitors, e.g., benzoylureas such as chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdyson antagonists such as halofenozide, methoxyfenozide, tebufenozide; c) juvenoids such as pyriproxyfen, methoprene, fenoxycarb; d) lipid biosynthesis inhibitors such as spirodiclofen;

neonicotinoids such as flonicamid, clothianidin, dinotefuran, imidacloprid, thiamethoxam, nitenpyram, nithiazin, acetamiprid, thiacloprid;

additionally unclassified insecticides such as abamectin, acequinocyl, acetamiprid, amitraz, azadirachtin, bensultap, bifenazate, cartap, chlorfenapyr, chlordimeform, cyromazine, diafenthiuron, dinetofuran, diofenolan, emamectin, endosulfan, ethiprole, fenazaquin, fipronil, formetanate, formetanate hydrochloride, gamma-HCH hydramethylnon, imidacloprid, indoxacarb, isoprocarb, metolcarb, pyridaben, pymetrozine, spinosad, tebufenpyrad, thiamethoxam, thiocyclam, XMC, and xylylcarb.

N-Phenylsemicarbazones, as described by the general formula I in EP-A 462 456, particularly compounds of the general formula II

II in which $R^5$ and $R^6$ independently of one another are hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^4$ is $C_1$-$C_4$ alkoxy, $C_1$-$C_4$ haloalkyl or $C_1$-$C_4$ haloalkoxy, e.g., compound IV, in which $R^5$ is 3-$CF_3$ and $R^6$ is 4-CN and $R^4$ is 4-$OCF_3$.

IV

Examples of growth regulators which can be used are chlormequat chloride, mepiquat chloride, prohexadione-calcium or those from the group of the gibberellins. These include, for example, the gibberellins $GA_1$, $GA_3$, $GA_4$, $GA_5$ and $GA_7$ etc., and the corresponding exo-16,17-dihydrogibberellins, and also the derivatives thereof, examples being esters with $C_1$-$C_4$ carboxylic acids. Preference in accordance with the invention is given to exo-16,17-dihydro-$GA_5$ 13-acetate.

Preferred fungicides are, in particular, strobilurins, azoles, and 6-aryltriazolo[1,5-a]pyrimidines, as described by the general formula I in WO 98/46608, WO 99/41255 or WO 03/004465, for example, especially active ingredients of the general formula III,

III in which:
$R^x$ is a group $NR^7R^8$, or linear or branched $C_1$-$C_8$ alkyl optionally substituted by halogen, OH, $C_1$-$C_4$ alkoxy, phenyl or $C_3$-$C_6$ cycloalkyl, or is $C_2$-$C_6$ alkenyl, $C_3$-$C_6$ cycloalkyl, $C_3$-$C_6$ cycloalkenyl, phenyl or naphthyl, it being possible for the four last-mentioned radicals to have 1, 2, 3 or 4 substituents selected from halogen, OH, $C_1$-$C_4$ alkyl, $C_1$-$C_4$ haloalkoxy, $C_1$-$C_4$ alkoxy, and $C_1$-$C_4$ haloalkyl;

$R^7$ and $R^8$ independently of one another are hydrogen, $C_1$-$C_8$ alkyl, $C_1$-$C_8$ haloalkyl, $C_3$-$C_{10}$ cycloalkyl, $C_3$-$C_6$ halocycloalkyl, $C_2$-$C_8$ alkenyl, $C_4$-$C_{10}$ alkadienyl, $C_2$-$C_8$ haloalkenyl, $C_3$-$C_6$ cycloalkenyl, $C_2$-$C_8$ halocycloalkenyl, $C_2$-$C_8$ alkynyl, $C_2$-$C_8$ haloalkynyl or $C_3$-$C_6$ cycloalkynyl, or $R^7$ and $R^8$, together with the nitrogen atom to which they are attached, form five-to eight-membered heterocyclyl, which is attached via N and may comprise one, two or three further heteroatoms from the group O, N, and S, as ring members, and/or may carry one or more substituents from the group of halogen, $C_1$-$C_6$ alkyl, $C_1$-$C_6$ haloalkyl, $C_2$-$C_6$ alkenyl, $C_2$-$C_6$ haloalkenyl, $C_1$-$C_6$ alkoxy, $C_1$-$C_6$ haloalkoxy, $C_3$-$C_6$ alkenyloxy, $C_3$-$C_6$ haloalkenyloxy, (exo)-$C_1$-$C_6$ alkylene, and oxy-$C_1$-$C_3$ alkyleneoxy;

L is selected from halogen, cyano, $C_1$-$C_6$ alkyl, $C_1$-$C_4$ haloalkyl, $C_1$-$C_6$ alkoxy, $C_1$-$C_4$ haloalkoxy, and $C_1$-$C_6$ alkoxycarbonyl;

$L^1$ is halogen, $C_1$-$C_6$ alkyl or $C_1$-$C_6$ haloalkyl, and especially fluorine or chlorine;

$X^2$ is halogen, $C_1$-$C_4$ alkyl, cyano, $C_1$-$C_4$ alkoxy or $C_1$-$C_4$ haloalkyl, and preferably is halogen or methyl, and in particular is chlorine.

Examples of compounds of the formula III are
5-chloro-7-(4-methylpiperidin-1-yl)-6-(2,4,6-trifluorophenyl)-[1,2,4]triazolo[1,5-a]pyrimidine, 5-chloro-7-(4-methylpiperazin-1-yl)-6-(2,4,6-trifluorophenyl)-[1,2,4]triazolo[1,5-a]pyrimidine, 5-chloro-7-(morpholin-1-yl)-6-(2,4,6-trifluorophenyl)-[1,2,4]triazolo[1,5-a]pyrimidine,
5-chloro-7-(piperidin-1-yl)-6-(2,4,6-trifluorophenyl)-[1,2,4]triazolo[1,5-a]pyrimidine,
5-chloro-7-(morpholin-1-yl)-6-(2,4,6-trifluorophenyl)-[1,2,4]triazolo[1,5-a]pyrimidine,
5-chloro-7-(isopropylamino)-6-(2,4,6-trifluorophenyl)-[1,2,4]triazolo[1,5-a]pyrimidine,
5-chloro-7-(cyclopentylamino)-6-(2,4,6-trifluorophenyl)-[1,2,4]triazolo[1,5-a]pyrimidine,
5-chloro-7-(2,2,2-trifluoroethylamino)-6-(2,4,6-trifluorophenyl)-[1,2,4]triazolo[1,5-a]-pyrimidine,
5-chloro-7-(1,1,1-trifluoropropan-2-ylamino)-6-(2,4,6-trifluorophenyl)-[1,2,4]triazolo[1,5-a]pyrimidine,
5-chloro-7-(3,3-dimethylbutan-2-ylamino)-6-(2,4,6-trifluorophenyl)-[1,2,4]triazolo[1,5-a]-pyrimidine,
5-chloro-7-(cyclohexylmethyl)-6-(2,4,6-trifluorophenyl)-[1,2,4]triazolo[1,5-a]pyrimidine,
5-chloro-7-(cyclohexyl)-6-(2,4,6-trifluorophenyl)-[1,2,4]triazolo[1,5-a]pyrimidine,
5-chloro-7-(2-methylbutan-3-yl)-6-(2,4,6-trifluorophenyl)-[1,2,4]triazolo[1,5-a]pyrimidine,
5-chloro-7-(3-methylpropan-1-yl)-6-(2,4,6-trifluorophenyl)-[1,2,4]triazolo[1,5-a]pyrimidine,
5-chloro-7-(4-methylcyclohexan-1-yl)-6-(2,4,6-trifluorophenyl)-[1,2,4]triazolo[1,5-a]-pyrimidine,
5-chloro-7-(hexan-3-yl)-6-(2,4,6-trifluorophenyl)-[1,2,4]triazolo[1,5-a]pyrimidine,
5-chloro-7-(2-methylbutan-1-yl)-6-(2,4,6-trifluorophenyl)-[1,2,4]triazolo[1,5-a]pyrimidine,
5-chloro-7-(3-methylbutan-1-yl)-6-(2,4,6-trifluorophenyl)-[1,2,4]triazolo[1,5-a]pyrimidine,
5-chloro-7-(1-methylpropan-1-yl)-6-(2,4,6-trifluorophenyl)-[1,2,4]triazolo[1,5-a]pyrimidine, 5-methyl-7-(4-methylpiperidin-1-yl)-6-(2,4,6-trifluorophenyl)-[1,2,4]triazolo[1,5-a]-pyrimidine,
5-methyl-7-(4-methylpiperazin-1-yl)-6-(2,4,6-trifluorophenyl)-[1,2,4]triazolo[1,5-a]-pyrimidine,
5-methyl-7-(morpholin-1-yl)-6-(2,4,6-trifluorophenyl)-[1,2,4]triazolo[1,5-a]pyrimidine,
5-methyl-7-(piperidin-1-yl)-6-(2,4,6-trifluorophenyl)-[1,2,4]triazolo[1,5-a]pyrimidine,
5-methyl-7-(morpholin-1-yl)-6-(2,4,6-trifluorophenyl)-[1,2,4]triazolo[1,5-a]pyrimidine,
5-methyl-7-(isopropylamino)-6-(2,4,6-trifluorophenyl)-[1,2,4]triazolo[1,5-a]pyrimidine,
5-methyl-7-(cyclopentylamino)-6-(2,4,6-trifluorophenyl)-[1,2,4]triazolo[1,5-a]pyrimidine,
5-methyl-7-(2,2,2-trifluoroethylamino)-6-(2,4,6-trifluorophenyl)-[1,2,4]triazolo[1,5-a]-pyrimidine,
5-methyl-7-(1,1,1-trifluoropropan-2-ylamino)-6-(2,4,6-trifluorophenyl)-[1,2,4]triazolo[1,5-a]pyrimidine,
5-methyl-7-(3,3-dimethylbutan-2-ylamino)-6-(2,4,6-trifluorophenyl)-[1,2,4]triazolo[1,5-a]-pyrimidine,
5-methyl-7-(cyclohexylmethyl)-6-(2,4,6-trifluorophenyl)-[1,2,4]triazolo[1,5-a]pyrimidine,
5-methyl-7-(cyclohexyl)-6-(2,4,6-trifluorophenyl)-[1,2,4]triazolo[1,5-a]pyrimidine,
5-methyl-7-(2-methylbutan-3-yl)-6-(2,4,6-trifluorophenyl)-[1,2,4]triazolo[1,5-a]pyrimidine,
5-methyl-7-(3-methylpropan-1-yl)-6-(2,4,6-trifluorophenyl)-[1,2,4]triazolo[1,5-a]pyrimidine,
5-methyl-7-(4-methylcyclohexan-1-yl)-6-(2,4,6-trifluorophenyl)-[1,2,4]triazolo[1,5-a]-pyrimidine,
5-methyl-7-(hexan-3-yl)-6-(2,4,6-trifluorophenyl)-[1,2,4]triazolo[1,5-a]pyrimidine,
5-methyl-7-(2-methylbutan-1-yl)-6-(2,4,6-trifluorophenyl)-[1,2,4]triazolo[1,5-a]pyrimidine, 5-methyl-7-(3-methylbutan-1-yl)-6-(2,4,6-trifluorophenyl)-[1,2,4]triazolo[1,5-a]pyrimidine and 5-methyl-7-(1-methylpropan-1-yl)-6-(2,4,6-trifluorophenyl)-[1,2,4]triazolo[1,5-a]pyrimidine.

Suitable insecticides are, in particular
arylpyrroles such as chlorfenapyr,
pyrethroids such as bifenthrin, cyfluthrin, cyproprothrin, cypermethrin, deltamethrin, esfenvalerate, ethofenprox, fenpropathrin, fenvalerate, cyhalothrin, lambda-cyhalothrin, permethrin, silafluofen, tau-fluvalinate, tefluthrin, tralomethrin, α-cypermethrin, zeta-cypermethrin and permethrin,
fipronil,
neonicotinoids and
semicarbazones of the formula II.

Suitable fluorescent agents are, for example, pyrene, uranin, rhodamine, fluorescein, coumarin, allophycocyanine, naphthalene, anthracene.

In one embodiment of the present invention the process according to the invention can be used to solubilize in the range from 0.01% to 1% by weight of hydrophobic active ingredient in aqueous medium, preferably at least 0.1% by weight, based on overall aqueous formulation prepared in accordance with the invention.

To perform the process according to the invention, one or more assistants are used, at least one of which is a hyperbranched polymer (A) which is defined in detail below and, in the context of the present invention, is also referred to for short as hyperbranched polymer (A), polymer (A), inventive hyperbranched polymer (A) or inventive polymer (A).

In one embodiment of the present invention, hyperbranched polymer (A) has a mean molecular weight $M_w$ in the range from 1000 to 100 000 g/mol, preferably 1500 to 50 000 g/mol. The mean molecular weight can be determined, for example, by gel permeation chromatography (GPC).

In one embodiment of the present invention, hyperbranched polymer (A) has a polydispersity ($M_w/M_n$) in the range from 1 to 50, preferably 1.1 to 30, more preferably 2 to 15.

Polymer (A) is obtainable by reacting at least one hyperbranched polymeric compound having at least one primary or secondary amino group per molecule (a), also referred to in the context of the present invention as hyperbranched compound (a) for short, which is selected from
(a1) hyperbranched polyamides and
(a2) hyperbranched polyureas,
with
(b) at least one mono-, di- or oligosaccharide.

Hyperbranched compounds (a) and therefore also the hyperbranched polymers (A) prepared therefrom are molecularly and structurally inhomogeneous. They differ from dendrimers, for example, by their molecular inhomogeneity and can be prepared with a considerably lower degree of complexity. One example of the molecular structure of a hyperbranched compound based on an $AB_2$ molecule can be found, for example, in WO 04/20503 on page 2. For the structure (distribution of the branches, etc.), the same applies to the polymers based on an $A_2+B_y$ strategy (where y≥3), used, for example, in the context of the present application; see, for example, J.-F. Stumbé et al., *Macromol. Rapid Commun.* 2004, 25, 921. For a definition of dendrimers and hyperbranched polymers see also P. J. Flory, *J. Am. Chem. Soc.* 1952, 74, 2718 and H. Frey et al., *Chemistry—A European J.* 2000, 6(14), 2499.

In the context of the present invention, hyperbranched is preferably understood to mean those polymeric compounds (a) or polymers (A) which have a degree of branching DB in the range from 10 to 99.9%, preferably 20 to 90% and more preferably up to 80%.

The degree of branching DB is defined as $$DB[\%]=100\cdot(T+Z)/(T+Z+L)$$

where T is the mean number of terminal monomer units, Z denotes the mean number of branched monomer units and L denotes the mean number of linear monomer units, in each case per molecule of polymeric compound (a) or polymer (A). For a definition of DB see H. Frey et al., *Acta Polym.* 1997, 48, 30.

In the context of the present invention, amino groups are understood to mean primary amino groups, i.e. $NH_2$ groups, or secondary amino groups, preferably $NHR^9$ groups with $R^9$ selected from $C_1$-$C_6$-alkyl, especially methyl or ethyl, or $C_3$-$C_7$-cycloalkyl or $C_1$-$C_6$-alkylene-$NH_2$, preferably $C_2$-$C_4$-alkylene-$NH_2$ or $C_2$-$C_4$-alkylene-(NH—$C_2$-$C_4$-alkylene)$_w$-$NH_2$ or $C_3$-$C_7$-cycloalkylene-$NH_2$, where w is in the range from 1 to 10, preferably in the range from 1 to 3, and preferred $C_2$-alkylene is $(CH_2)_2$, which may be incorporated anywhere in a hyperbranched polyamide (a1) or hyperbranched polyurea (a2).

Examples of $R^9$ are methyl, $CH_2$—$NH_2$, ethyl, $CH_2$—$CH_2$—$NH_2$, propyl, $(CH_2)_3$—$NH_2$, butyl, $(CH_2)_4$—$NH_2$, n-hexyl, $(CH_2)_6$—$NH_2$, cyclohexyl and para-cyclohexylene-$NH_2$.

Hyperbranched polyamide (a1) or hyperbranched polyurea (a2) may have only primary amino groups or only secondary amino groups or primary and secondary amino groups.

In one embodiment of the present invention, hyperbranched polyamide (a1) or hyperbranched polyurea (a2) has at least two primary or secondary amino groups per molecule.

In the context of the present invention, hyperbranched polyamides (a1) are understood to mean those hyperbranched polyamides which can be prepared by polycondensing monomers $A_2$ and $B_3$, where $A_2$ can be understood to mean, for example, dicarboxylic acids or suitable derivatives such as mono- or di-$C_1$-$C_4$-alkyl esters of dicarboxylic acids or anhydrides, and $B_3$ can be understood to mean trifunctional or higher-functionality amines, variant (A), where aforementioned trifunctional or higher-functionality amines are selected from compounds which have 3 or more than 3 amino groups per molecule, selected from primary and secondary amino groups, preferably from $NH_2$ groups and $NHR^9$ groups. Trifunctional or higher-functionality amines may, in addition to the primary or secondary amino groups, also have further functional groups, for example tertiary amino groups.

Dicarboxylic acids used with preference as monomer $A_2$ are, for example, oxalic acid, malonic acid, succinic acid, glutaric acid, adipic acid, pimelic acid, suberic acid, sebacic acid, undecane-α,ω-dicarboxylic acid, cis- and trans-cyclohexane-1,2-dicarboxylic acid, cis- and trans-cyclohexane-1,3-dicarboxylic acid, cis- and trans-cyclohexane-1,4-dicarboxylic acid and derivatives thereof, such as mono- and dialkyl esters, acid chlorides or anhydrides.

Preferred trifunctional or higher-functionality primary or secondary amines are, for example, tris(2-aminoethyl)amine, tris(2-aminopropyl)amine, diethylenetriamine, triethylenetetraamine, tetraethylenepentamine, bis(hexamethylene)triamine and derivatives thereof, and alkoxylated and aminated higher-functionality alcohols, for example Jeffamine® T products.

Jeffamine® T are trifunctional polyetherpolyols with terminal primary amino groups. They are prepared proceeding from a trifunctional alcohol initiator which is reacted with ethylene oxide and/or propylene oxide, the terminal hydroxyl groups of which, obtained in this step, are subsequently converted to amino groups.

In another embodiment, $A_2$ is understood to mean, for example, diamines, and $B_3$ to mean trifunctional or higher-functionality polycarboxylic acids or derivatives thereof, such as anhydrides, mono-, di- or tri-$C_1$-$C_4$-alkyl esters of trifunctional or higher-functionality polycarboxylic acids, variant (B).

Preferred diamines are, for example, ethylenediamine, propylenediamines (1,2-diaminopropane and 1,3-diaminopropane), 1,4-diaminobutane, 1,5-diaminopentane, 1,6-diaminohexane, 1,8-diaminooctane and isophoronediamine.

Suitable trifunctional or higher-functionality carboxylic acids are, for example, trimesic acid, trimellitic acid, pyromellitic acid, butanetricarboxylic acid and cyclohexane-1,3,5-tricarboxylic acid and derivatives thereof, such as mono- and dialkyl esters, acid chlorides or anhydrides.

In another embodiment of the present invention, hyperbranched polyamides (a1) are understood to mean those hyperbranched polyamides which can be obtained by self-condensation of functional carboxylic acids, for example of the $AB_2$ type, where, in the case of hyperbranched polyamides (a1), A represents a carboxylic acid having two identical or different functional B groups. B in this context may be selected, for example, from OH, SH and $NH_2$. $B_2$ preferably represents two $NH_2$ groups. Examples of suitable functional carboxylic acids of the $AB_2$ type are cysteine, serine and especially lysine.

In another embodiment of the present invention, hyperbranched polyamides (a1) are understood to mean those hyperbranched polyamides which can be obtained by self-condensation of functional carboxylic acids, for example of the $AB_2$ type, where, in the case of hyperbranched polyamides (a1), B represents a carboxylic acid with a further functional A group other than COOH. A in this context may, for example, be selected from OH, SH and $NH_2$. Examples of such suitable functional carboxylic acids of the $AB_2$ type are glutamic acid and aspartic acid.

Amino acids can be used in each case as racemates or in enantiomerically pure form, especially as the L isomer.

Hyperbranched polyamides (a1) may comprise one or more further compounds incorporated by condensation, for example one or more aliphatic or aromatic or cycloaliphatic diamines in the case of variant (A) or, for example, one or more dicarboxylic acids in the case of variant (B).

In one embodiment of the present invention, hyperbranched polyamides (a1) have a mean molecular weight $M_w$ in the range from 800 to 100 000 g/mol, preferably in the range from 1000 to 75 000 g/mol.

Hyperbranched polyamides (a1) and processes for preparation thereof are disclosed, for example, in WO 2006/018125 and the literature cited therein.

In one embodiment of the present invention, hyperbranched polyamides (a1) are selected from hyperbranched polylysines (a3).

In the context of the present invention, hyperbranched polylysines (a3) are understood to mean uncrosslinked polymers which have lysine as a monomer unit.

In one embodiment of the present invention, hyperbranched polylysine (a3) may have up to 20 mol % of monomer units other than lysine, for example aspartic acid or glutamic acid or one or more other dicarboxylic acids, for example adipic acid or succinic acid.

In one embodiment of the present invention, hyperbranched polylysines (a3) have a mean molecular weight $M_w$ in the range from 1000 to 750 000 g/mol, preferably in the range from 3000 to 100 000 g/mol.

In one embodiment of the present invention, hyperbranched polylysine (a3) may have a degree of branching in the range from 10 to 99.9%, preferably 20 to 99% and more preferably up to 95%.

In the context of the present invention, "uncrosslinked" in the context of hyperbranched polylysine (a3) is understood to mean that it has a lower degree of crosslinking than polylysines which have the same molecular weight $M_w$ and are obtainable by polycondensation of free lysine base.

One measure of the degree of crosslinking is, for example, a comparison of the gel content of the polylysines in question, i.e. the proportion which is insoluble in the course of storage under water at a temperature of 23° C. for twenty-four hours, converted to percent.

Hyperbranched polylysines (a3) and processes for preparation thereof are disclosed, for example, in WO 2007/060119.

In the context of the present invention, the term "hyperbranched polyureas" (a2) also comprises substances which, in addition to urea groups, may also have urethane groups and optionally further functional groups, for example amino groups. Urethane groups are preferably O-alkyl- or O-alkenylurethane groups, where the alkyl or alkenyl radical has one to 18 carbon atoms. Preference is given to O-alkylurethane groups which are obtainable by reaction of an isocyanate group with a monoalcohol which has been used as a blocking agent.

Hyperbranched polyureas (a2) are obtainable by various routes, for example by direct reaction of isocyanates with polyamines, of urea with polyamines, or by reaction of dialkyl carbonates with polyamines. In the context of the present invention, hyperbranched polyureas (a2), however, are preferably obtainable by reacting a blocked polyisocyanate with polyamines, as in WO 03/066702. Further preparation processes are described; for example, WO 2005/044897 A1 describes the synthesis of suitable hyperbranched polyureas (a2) from organic carbonates, e.g. diethyl carbonate ($A_2$ monomer), and polyfunctional amines, e.g. triamines ($B_3$ monomers). WO 2005/075541 describes the synthesis of hyperbranched polyureas from urea or urea derivatives ($A_2$ monomers) and polyfunctional amines, e.g. triamines ($B_3$ monomers).

Hyperbranched polyureas (a2) are preferably obtainable by a process comprising the reaction of an at least difunctional blocked di- or polyisocyanate with at least one at least difunctional primary and/or secondary amine with elimination of the blocking agent.

The at least difunctional blocked di- or polyisocyanates required as starting materials can be prepared, for example, by reaction of di- or polyisocyanates with aliphatic, araliphatic or aromatic alcohols, preferably monoalcohols.

Suitable monoalcohols are preferably linear or branched aliphatic monoalcohols, such as methanol, ethanol, propanol, butanol, pentanol, hexanol, heptanol, octanol, isopropanol, isobutanol or 2-ethyl-1-hexanol or araliphatic monoalcohols, such as benzyl alcohol or phenylethanol. Particular preference is given to the linear or branched aliphatic monoalcohols, and also benzyl alcohol. Especially preferred are linear aliphatic monoalcohols having 1 to 18, preferably 1 to 6, carbon atoms.

At least difunctional amines used in the preparation of hyperbranched polyureas (a2) are selected from compounds which bear at least two amine groups reactive with urethane groups. Compounds having at least two amine groups reactive with urethane groups are, for example, ethylenediamine, N-alkylethylenediamine, propylenediamine, 2,2-dimethyl-1,3-propanediamine, N-alkylpropylenediamine, butylenediamine, N-alkylbutylenediamine, hexamethylenediamine, N-alkylhexamethylenediamine, tolylenediamine, diaminodiphenylmethane, diaminodicyclohexylmethane, phenylenediamine, cyclohexyldiamine, diaminodiphenyl sulfone, isophoronediamine, 2-butyl-2-ethyl-1,5-pentamethylenediamine, 2,2,4- or 2,4,4-trimethyl-1,6-hexamethylene-diamine, 2-aminopropylcyclohexylamine, 3(4)-aminomethyl-1-methylcyclohexylamine, 1,4-diamino-4-methylpentane, amine-terminated polyoxyalkylenepolyols (for example Jeffamine® from Huntsman Corporation), aminated polytetramethylene glycols, N-aminoalkylpiperidines, ammonia, bis(aminoethyl)amine, bis(aminopropyl)amine, bis (aminobutyl)amine, bis(aminopentyl)amine, bis(aminohexyl)amine, tris(aminoethyl) amine, tris(aminopropyl) amine, tris(aminohexyl)amine, trisaminohexane, 4-aminomethyl-1,8-octamethylenediamine, N'(3-aminopropyl)-N,N-dimethyl-1,3-propanediamine, trisaminononane or melamine. In addition, it is also possible to use any desired mixtures of at least two of the compounds mentioned. Preferred at least difunctional primary and/or secondary amines are at least difunctional primary amines, more preferably difunctional aliphatic primary amines, especially isophoronediamine.

Useful di- or polyisocyanates include aliphatic, cycloaliphatic, araliphatic and aromatic di- and polyisocyanates known per se. These preferably include 4,4'-diphenylmethane diisocyanate, mixtures of monomeric diphenylmethane diisocyanates and oligomeric diphenylmethane diisocyanates (polymer MDI), tetramethylene diisocyanate, tetramethylene diisocyanate trimers, hexamethylene diisocyanate, hexamethylene diisocyanate trimers, isophorone diisocyanate (IPDI), isophorone diisocyanate trimer, 2,4-tolylene diisocyanate (2,4-TDI), 2,4'-diphenylmethane diisocyanate (2,4'-MDI), 2,6-tolylene diisocyanate (2,6-TDI) or triisocyanatotoluene.

For formation of hyperbranched polyureas (a2), particular preference is given to the following:

Di- or polyisocyanates, especially oligo- or polyisocyanates, which can be prepared from aliphatic, cycloaliphatic, araliphatic and aromatic, preferably aliphatic, di- or polyisocyanates by linkage by means of urethane, allophanate, urea, biuret, uretdione, amide, isocyanurate, carbodiimide, uretonimine, oxadiazinetrione or iminooxadiazinedione structures, preferably by means of isocyanurate structures. Typically, these oligo- or polyisocyanates have a mean NCO functionality of 2.1 to 4.9, preferably 2.9 to 4.4, especially of 3.4 to 3.9. The mean molar mass $M_w$ is preferably in the range from 300 to 3000 g/mol, preferably from 400 to 1500 g/mol, especially from 500 to 800 g/mol.

In one embodiment of the present invention, the hyperbranched polyureas (a2) selected are those which have been synthesized with addition, in the course of the synthesis, of monofunctional aliphatic, araliphatic or aromatic amines as chain terminators. Suitable monofunctional amines are primary alkylamines, preferably $C_1$-$C_{18}$-alkylamines, and more preferably Jeffamine® M products (M1000 and M2010).

Jeffamine® M products are monofunctional polyetherpolyols from Huntsman Corporation with terminal primary amino groups. They are prepared proceeding from a monoalcohol initiator which is reacted with ethylene oxide and/or propylene oxide, and whose terminal hydroxyl group obtained in this step is subsequently converted to an amino group.

In one embodiment, hyperbranched polyamides (a1) and hyperbranched polyureas (a2) have such a structure that they are not water-soluble per se, i.e. less than 1 g/l is soluble in water at 23° C., preferably less than 0.1 g/l.

Above-described polymeric compound (a) is reacted with (b) at least one mono-, di- or oligosaccharide, also referred to
  individually in the context of the present invention as
  monosaccharide (b), disaccharide (b) and oligosaccharide
  (b), or else collectively as saccharide (b) for short,
  selecting those reactions by which saccharide (b) is linked
to polymeric compound (a).

In the context of the present invention, monosaccharides (b) are understood to mean natural or synthetic monosugars which may have one or more protecting groups, for example acetyl, benzyl or acetonide. Monosaccharides (b) preferably do not have any protecting groups.

Preferred monosaccharides (b) are pentoses, for example arabinose, xylose or ribose, and hexoses, especially galactose, mannose or glucose, and additionally hexyloses such as fructose and sorbose.

In the context of the present invention, disaccharides (b) are understood to mean natural or synthetic disugars which may have one or more protecting groups, for example acetyl, benzyl or acetonide. Disaccharides (b) preferably do not have any protecting groups.

Preferred disaccharides are crystal sugar, lactose and maltose.

In the context of the present invention, oligosaccharides (b) are understood to mean natural or synthetic polysugars having three to 50, preferably up to 25 and more preferably up to 20 monosaccharide units per molecule, which may have one or more protecting groups, for example acetyl, benzyl or acetonide. Oligosaccharides (b) preferably do not have any protecting groups.

Oligosaccharides (b) are generally water-soluble; for example, at least 10 g/l dissolve in distilled water at 20° C. and standard pressure, preferably at least 20 g/l, more preferably at least 100 g/l.

Saccharide (b) may preferably be present as the hydrate.

Particularly preferred saccharides (b) are monosaccharides (b), disaccharides (b) and oligosaccharides (b) having 3 saccharide units per molecule, i.e. trisaccharides (b).

In disaccharides (b) and oligosaccharides (b), the saccharide units may each be the same or different. In oligosaccharides, the saccharide units may also be essentially the same, for example glucose units, and only some, for example up to 10 mol %, preferably up to 20 mol %, are not glucose units.

In disaccharide (b) or oligosaccharide (b), the saccharide units are preferably joined to one another by glycosidic bonds.

In one embodiment of the present invention, in polymer (A) mono-, di-, or oligosaccharide (b) is bonded glycosidically to hyperbranched polymeric compound (a), especially via an amino group. In the context of the present invention, "glycosidic" means that the bond is via the aldehyde function or the ketone function of the saccharide (b) in question. The glycosidic bond may have been formed reversibly or irreversibly.

In one embodiment of the present invention, different saccharides (b) are bonded to the same hyperbranched polymer (a). Different saccharides may, for example, be a disaccharide (b) and an oligosaccharide (b) which are derived from the same sugar unit, for example from glucose or from mannose, or a monosaccharide (b) and a disaccharide (b) which are derived from the same sugar unit, or a monosaccharide (b) and an oligosaccharide (b) which are derived from the same sugar unit. In one variant, different saccharides (b) are bonded to the same hyperbranched polymer (a), for example two different monosaccharides (b) or two different disaccharides (b) or two different polysaccharides (b).

In one embodiment of the present invention, an average of at least one terminal amino group per molecule of hyperbranched polymeric compound (a) is bonded to one molecule of saccharide (b); preferably, at least two amino groups per molecule of hyperbranched polymeric compound (a) are each bonded to one molecule of saccharide (b).

In one embodiment of the present invention, the primary or secondary amino groups of hyperbranched polymeric compound (a) are joined quantitatively to saccharide (b), preferably to an extent of at least 90 mol %.

In another embodiment of the present invention, 10 to 90 mol % of the primary or secondary amino groups of hyperbranched polymeric compound (a) are joined to saccharide (b).

$NH_2$ groups joined quantitatively to saccharide (b) are joined to two molecules of saccharide (b) per $NH_2$ group.

$NHR^9$ groups joined quantitatively to saccharide (b) are joined to one molecule of saccharide (b) per $NHR^9$ group.

When polymeric compound (a) is joined quantitatively to saccharide (b), this means that two molecules of saccharide (b) are joined to each $NH_2$, and one molecule of saccharide (b) to each $NHR^9$ group.

In one embodiment of the present invention, inventive hyperbranched polymer (A) is contacted with one or more hydrophobic active ingredients and aqueous medium, for example by mixing. The mixing can be executed, for example, by stirring with conventional stirrers or with high-speed stirrers. Further suitable methods are the application of ultrasound or vigorous shaking. The mixing is effected preferably in more than one stage, by, for example, first contacting inventive hyperbranched polymer (A) with aqueous medium and then with one or more hydrophobic active ingredients.

In one embodiment of the present invention, hyperbranched polymer (A) and hydrophobic active ingredient are used in a mass ratio in the range from 1:1 to 1000:1, preferably 1:1 to 100:1.

In one embodiment, hyperbranched polymer (A) is stirred with aqueous medium and then with one or more active ingredients.

The mixing can be effected at temperatures in the range from 0° C. to 100° C. and—if there is a wish to employ elevated pressure—also at temperatures up to, for example, 150° C. Preference is given to working under standard pressure and at temperatures in the range from 15 to 70° C., preferably in the range from 20 to 50° C.

In one embodiment of the present invention, after the mixing has ended, unsolubilized hydrophobic active ingredient is removed, for example by filtration or centrifugation.

The present invention further provides hyperbranched polymers (A) which are soluble or dispersible in water, i.e. water-soluble or water-dispersible hyperbranched polymers (A), which are obtainable by reacting at least one hyperbranched polymeric compound (a) selected from (a1) hyperbranched polyamides and
(a2) hyperbranched polyureas,
with
(b) at least one mono-, di- or oligosaccharide.

The process according to the invention for solubilization can be conducted particularly efficiently with inventive polymers (A).

In connection with inventive polymer (A), "water-soluble" or "soluble in water" means that at least 10 g/l dissolve in distilled water at 20° C. and standard pressure, preferably at least 20 g/l, more preferably at least 100 g/l.

"Water-dispersible" polymers are understood to mean those polymers (A) which do not dissolve in water but which can be processed to dispersions which, at room temperature, do not form any sediment perceptible to the naked eye within at least two hours. Polymers (A) bound to stationary phases in columns are not water-dispersible in the context of the present invention.

The remaining terms are each as defined above.

In one embodiment of the present invention, oligosaccharides (b) are selected from compounds formed from three to 20 monosaccharide units per molecule which may be the same or different.

In one embodiment of the present invention, inventive hyperbranched polymers (A) have a mean molecular weight $M_w$ in the range from 1000 to 100 000 g/mol, preferably 1500 to 50 000 g/mol. The mean molecular weight can be determined, for example, by gel permeation chromatography (GPC).

In one embodiment of the present invention, inventive hyperbranched polymer (A) has a polydispersity ($M_w/M_n$) in the range from 1.1 to 30 and more preferably from 2 to 15.

In one embodiment of the present invention, mono-, di- or oligosaccharide (b) is bonded glycosidically to hyperbranched polymeric compound (a), especially via an amino group.

In one embodiment of the present invention, hyperbranched polyamides (a1) are selected from hyperbranched polylysines (a3).

The present invention further provides a process for preparing inventive hyperbranched polymers (A), also referred to in the context of the present invention as preparation process according to the invention. In the preparation process according to the invention, at least one hyperbranched polymeric compound (a), selected from
(a1) hyperbranched polyamides and
(a2) hyperbranched polyureas,
is reacted with
(b) at least one mono-, di- or oligosaccharide
in the liquid phase under reductive amination conditions.

"In the liquid phase" is understood to mean that the reaction or linkage of hyperbranched polymeric compound (a) with saccharide (b) is performed in molten hyperbranched compound (a) or preferably in solution.

Suitable solvents are, for example, protic and aprotic organic solvents, for example tetrahydrofuran, dichloromethane, chloroform and alcohols, for example ethanol, isopropanol and methanol.

A particularly suitable solvent is water.

Reductive aminations are known per se. Without any intention to hereby give preference to a particular theory, the reductive amination in the present invention can be explained as a multistage reaction, wherein, in a first step, hyperbranched compound (a) having a primary or secondary amino group reacts with the aldehyde or keto group of saccharide (b) to form an imine selected from aldimines and ketimines, which is then reduced to an amine in a second step.

In one embodiment of the present invention, the reducing agents used are hydrides or hydride complexes, especially $LiBH_4$ or $NaBH_4$ or $NaBH_3CN$.

In one embodiment of the present invention, the reducing agent used is a borane-Lewis base complex. Suitable Lewis bases are, for example, thioethers, cyclic and noncyclic ethers and aliphatic or aromatic amines, and also heteroaromatics. Examples of thioethers are dimethyl sulfide and diethyl sulfide. Examples of suitable noncyclic ethers are especially bis-$C_2$-$C_{10}$-dialkyl ethers in which the alkyl radicals are different or preferably the same, for example diethyl ether, diisopropyl ether and di-n-butyl ether. Examples of cyclic ethers are tetrahydrofuran (THF) and tetrahydropyran. An example of aliphatic amines is tert-butylamine. Examples of tertiary amines are especially tri-$C_1$-$C_4$-alkylamines, for example triethylamine, and additionally bicyclic amines, for example [2,2,2]-diazabicyclooctane (Dabco). Examples of aromatic amines are especially tertiary aromatic amines such as N,N-dimethylaniline and N,N-diethylaniline. Examples of heteroaromatic compounds are especially pyridine, 2-picoline and 5-ethyl-2-methylpyridine.

In one embodiment of the present invention, the reducing agent selected is ascorbic acid in an acetic acid/acetate buffer.

In another embodiment, an acetic acid/acetate buffer without an additional reducing agent is selected to form the bond between saccharide (b) and amino group via an imine intermediate and subsequent reduction, known from D. Bandra, A. K. Yadav, S. Bhadra, N. K. Jain *International Journal of Pharmaceutics* 2005, 295, 221-233 and P. V. Kumar et al. *Journal of Drug Targeting* 2006, 14, 546-556.

Particular preference is given to selecting, as the Lewis base, heteroaromatic amines in which at least one nitrogen atom is part of the heteroaromatic system, for example pyridine, substituted by, for example, $C_1$-$C_4$ alkyl, or more preferably unsubstituted. Very particular preference is given to the borane-Lewis base complex $BH_3$.pyridine, also referred to in the literature as $BH_3$*Py for short.

In one embodiment of the present invention, hyperbranched polymeric compound (a) and saccharide (b) are used in such ratios that the molar ratio of primary or secondary amino groups to saccharide (b) is in the range of 1:0.5-1:20, preferably 1:1-1:10.

In one embodiment of the present invention, saccharide (b) and reducing agent are used in a molar ratio in the range from 1:1 to 1:3, most preferably in equimolar amounts.

In this reaction, it is possible to control, with the aid of an optionally used excess, which and how many amino groups are to be converted. If only the primary amino groups are to be converted, stoichiometric use of saccharide (b) and reducing agent is sufficient, based on primary amino groups. If secondary amino groups are also to be converted, reducing agent and saccharide (b) are each used in stoichiometric amounts relative to the sum of primary and secondary amino groups from hyperbranched polymeric compound (a). If all secondary amino groups are also to be converted, a high excess of reducing agent is required.

In one embodiment of the present invention, the preparation process according to the invention is performed at temperatures in the range from zero to 100° C., preferably 15 to 70° C.

A suitable reaction time has been found to be one hour to two weeks, the reaction time being selectable as a function of the temperature. The lower the temperature, the longer the reaction time selected.

The reaction pressure at which the preparation process according to the invention is performed is uncritical per se. Preference is given to selecting standard pressure.

In one embodiment of the present invention, the preparation process according to the invention is performed at a pH in the range from 3 to 10, preferably from 6 to 9 and more preferably from 8 to 9. To establish the pH, buffers known per se can be used, for example acetate buffer or borate buffer.

In one embodiment of the present invention, after the chemical reaction to prepare inventive hyperbranched polymer (A) has ended, a purification is dispensed with.

In another embodiment of the present invention, purification is effected after the chemical reaction to prepare inventive hyperbranched polymer (A) has ended. Such a purification may comprise, for example, the evaporation of solvent and released Lewis base. A purification may additionally include a removal of inorganic salts which originate, for example, from buffers used.

Workup can be conducted by methods known per se, for example by chromatography, reprecipitation, filtration, particle size-dependent separating processes, for example ultrafiltration, or by dialysis.

The present invention further provides complexes comprising at least one inventive hyperbranched polymer (A) and at least one hydrophobic active ingredient. Complexes shall be understood to mean not only complexes in the sense of complex theories but also inclusion compounds or other aggregates of hydrophobic active ingredient and inventive hyperbranched polymer (A), without any intention to give preference to a particular theory.

Inventive complexes may, for example, comprise one or more molecules of hydrophobic active ingredient and one or more molecules of inventive hyperbranched polymer (A), i.e. need not comprise exactly one molecule of hydrophobic active ingredient and exactly one molecule of inventive hyperbranched polymer (A). In addition, inventive complexes may comprise, in intercalated form, water or other constituents/additives present in the formulation.

The present invention further provides a process for preparing inventive complexes. The procedure for preparing inventive complexes may be to mix at least one hydrophobic active ingredient and at least one inventive hyperbranched polymer (A) with one another, for example by one of the aforementioned processes, preferably in the presence of water.

The present invention further provides aqueous formulations comprising at least one inventive complex, for example in concentrations of 0.01 to 400 g/l, more preferably of 0.015 to 100 g/l.

Inventive complexes and hence inventive aqueous formulations can—according to the hydrophobic active ingredient used—be utilized, for example, as crop protection agents or for production of medicaments.

The invention is illustrated by working examples.

Terms:

DBTL: di-n-butyltin dilaurate

Jeffamin® M-1000: monofunctional polyetherpolyol with terminal primary amino group, mean molar mass $M_w$ approx. 1000 g/mol, Huntsman Corporation General Remarks:

Hyperbranched polyamides (a1) and hyperbranched polyureas (a2) were analyzed by gel permeation chromatography with a refractometer as the detector. The mobile phase used was hexafluoroisopropanol (HFIP) or water; the standard used to determine the molecular weight was polymethyl methacrylate (PMMA).

The amine number was determined to DIN EN 13717.

The inventive hyperbranched polymers (A) were analyzed by gel permeation chromatography with a refractometer as the detector.

The dialyses were performed with dialysis membranes of the ZelluTrans/Roth V series from Carl Roth GmbH & Co, Karlsruhe/Germany. Types with MWCOs (molecular weight cut-offs) of 1000 g/mol were used, unless stated otherwise.

I. Preparation of Hyperbranched Polyamides (a1)

I.1 Preparation of Hyperbranched Polyamide (a1.1)

A reaction vessel which had been provided with stirrer, internal thermometer, reflux condenser and nitrogen inlet tube was initially charged with 362 g of tetraethylenepentamine. While stirring, 238 g of dimethyl adipate were metered in over a period of one hour such that the internal temperature was about 100° C. On completion of addition, the reaction mixture was heated to 140° C. and stirred at 140° C. for one hour. Then the reflux condenser was exchanged for a descending condenser with a collecting vessel and the distillative removal of the methanol released in the reaction was commenced. After 150 minutes, the amount of distillate collected was 17.1 g of methanol. Thereafter, the reaction was ended by cooling to room temperature. The hyperbranched polyamide (a1.1) thus obtained was obtained as a viscous yellow oil.

Analytical data (GPC in HFIP): $M_n$=6300 g/mol; $M_w$=14 300 g/mol

Amine numbers: primary amine: 120 mg KOH/g (a1.1), secondary amine: 381 mg KOH/g (a1.1).

I.2 Preparation of Hyperbranched Polyamide (a1.2)

A reaction vessel which had been provided with stirrer, internal thermometer, reflux condenser and nitrogen inlet tube was initially charged with 343.9 g of tris(2-aminoethyl) amine. While stirring, 256.1 g of dimethyl adipate were metered in over a period of two hours such that the internal temperature was about 100° C. On completion of addition, the reaction mixture was heated to 140° C. and stirred at 140° C. for 90 minutes. Then the reflux condenser was exchanged for a descending condenser with a collecting vessel and the distillative removal of the methanol released in the reaction was commenced. After 2 hours, the amount of distillate collected was 14.3 g of methanol. Thereafter, the reaction was ended by cooling to room temperature. The hyperbranched polyamide (a1.2) thus obtained was obtained as a viscous yellow oil.

Analytical data (GPC in HFIP): $M_n$=5400 g/mol; $M_w$=10 700 g/mol;

Amine numbers: primary amine: 346 mg KOH/g (a1.2), secondary amine: 50 mg KOH/g (a1.2).

I.3 Preparation of Hyperbranched Polyurea (a2.1)

Stage 1: A reaction vessel which was provided with stirrer, internal thermometer, reflux condenser and nitrogen inlet tube was initially charged with 1903.9 g of trimeric hexamethylene diisocyanate while sparging with dry nitrogen, and heated to 80° C. while stirring. Then 751.1 g of anhydrous n-butanol were added with constant stirring over a period of 5 hours such that the temperature of the reaction mixture did not exceed 80° C. After the addition had ended, the mixture was stirred at 80° C. for one hour and then cooled to room temperature.

Stage 2: In a reaction vessel which was provided with stirrer, internal thermometer, descending condenser with collecting vessel and nitrogen inlet tube, 255 g of the reaction product from stage 1 were admixed with 50.2 g of isophoronediamine, 294.8 g of Jeffamine® M-1000 and 0.1 g of DBTL while sparging with dry nitrogen. The reaction mixture was heated to 170° C. with constant stirring and stirred at 170° C. for 90 min, in the course of which n-butanol released in the reaction was distilled off. During the reaction, the amine consumption in the reaction mixture was monitored by titration of aliquots with 0.1N HCl and the conversion was thus determined in percent relative to the theoretically possible conversion. On attainment of a conversion of 68%, the mixture was cooled to room temperature which stopped the reaction. This afforded hyperbranched polyurea (a2.1) in the form of a yellow liquid of high viscosity.

Analytical data (GPC in HFIP): $M_n$=10 200 g/mol; $M_w$=37 700 g/mol;

Amine number: primary amine 26 mg KOH/g (a2.1).

I.4 Preparation of Hyperbranched Polylysine (a3.1)

In a reaction vessel which was provided with stirrer, internal thermometer, descending condenser with collecting vessel and nitrogen inlet tube, 1000 g of L-lysine monohydrochloride were admixed with 219.1 g of NaOH, 150 g of water and 0.1 g of DBTL. The reaction mixture was heated to 150° C. while stirring and stirred at 150° C. over a period of 5.5 h, in the course of which water formed distilled out of the reaction mixture. Once 312 g of water had distilled off, the pressure in the reaction vessel was lowered to 200 mbar and the temperature was increased to 170° C. in order to distil off further water. The mixture was stirred at 170° C. for 30 minutes and then cooled to room temperature, which stopped the reaction.

Hyperbranched polylysine (a3.1) was obtained as a yellow solid.

Analytical data (GPC in water): $M_n$=14 300 g/mol, $M_w$=118 000 g/mol,

Amine number=n.d.

I.5 Preparation of Hyperbranched Polylysine (a3.2)

In a reaction vessel which was provided with stirrer, internal thermometer, descending condenser with collecting vessel and nitrogen inlet tube, 1000 g of L-lysine monohydrochloride were admixed with 219.1 g of NaOH, 150 g of water and 0.1 g of DBTL. The reaction mixture was heated to 150° C. while stirring and stirred at 150° C. over a period of 5.5 h, in the course of which water formed distilled out of the reaction mixture. Once 230 g of water had distilled off, the pressure in the reaction vessel was lowered to 200 mbar and the temperature was increased to 170° C. in order to distil off further water. The mixture was stirred at 170° C. for 30 minutes and then cooled to room temperature, which stopped the reaction.

Analytical data (GPC in HFIP): $M_n$=1370 g/mol, $M_w$=2800 g/mol,
Amine number=378 mg KOH/g (a3.2)

II. Preparation of Inventive Hyperbranched Polymers (A)

II.1 Preparation of Inventive Hyperbranched Polymer (A1.2-1-1)

In a 1 l flask, 10 g of hyperbranched polyamide (a1.2), corresponding to 61.8 mmol of $NH_2$ groups, were dissolved in 350 ml of aqueous 0.1 M sodium borate buffer and the mixture was stirred at room temperature for one hour. Then 222.7 g (618 mmol) of D(+)-maltose (b.1) were added while stirring vigorously. Then the mixture was heated to 50° C. In the course of this, complete dissolution of the D(+)-maltose (b.1) was achieved. After adding 77.3 ml of an 8 M solution of borane-pyridine complex in THF (618 mmol), the reaction mixture was stirred at 50° C. for 7 days. The reaction mixture was dialyzed for 4 days against double-distilled water, and the product obtained was freeze-dried. Inventive hyperbranched polymer (A1.2-1-1) was obtained as a white amorphous product with a yield of 20% (10 g).

II.2 Preparation of Inventive Hyperbranched Polymer (A1.2-1-2)

In a 1 l flask, 10 g of hyperbranched polyamide (a1.2), corresponding to 61.8 mmol of $NH_2$ groups, were dissolved in 100 ml of aqueous 0.1 M sodium borate buffer and the mixture was stirred at room temperature for one hour. Then 22.3 g (61.8 mmol) of D(+)-maltose (b.1) were added while stirring vigorously. Then the mixture was heated to 50° C. In the course of this, complete dissolution of the D(+)-maltose (b.1) was achieved. After adding 7.8 ml of an 8 M solution of borane-pyridine complex in THF (61.8 mmol), the reaction mixture was stirred at 50° C. for 7 days. The reaction mixture was dialyzed for 4 days against double-distilled water, and the product obtained was freeze-dried. Inventive hyperbranched polymer (A1.2-1-2) was obtained as a white amorphous product with a yield of 10% (3.2 g).

II.3 Preparation of Inventive Hyperbranched Polymer (A3.1-1-1)

In a 1 l flask, 5 g of hyperbranched polylysine (a3.1) were dissolved in 350 ml of aqueous 0.1 M sodium borate buffer and the mixture was stirred at room temperature for a half hour. Then 277 g (769 mmol) of D(+)-maltose (b.1) were added while stirring vigorously. Then the mixture was heated to 50° C. In the course of this, complete dissolution of the D(+)-maltose (b.1) was achieved. After adding 96 ml of an 8 M solution of borane-pyridine complex in THF (769 mmol), the reaction mixture was stirred at 50° C. for 7 days. The reaction mixture was dialyzed for 4 days against double-distilled water, and the product obtained was freeze-dried. Inventive hyperbranched polymer (A3.1-1-1) was obtained as a white amorphous product with a yield of 30% (18.1 g).

II.4 Preparation of Inventive Hyperbranched Polymer (A3.1-1-2)

In a 1 l flask, 5 g of hyperbranched polylysine (a3.1) were taken up in 50 ml of aqueous 0.1 M sodium borate buffer and the mixture was stirred at room temperature for a half hour. Then 27.7 g (76.9 mmol) of D(+)-maltose (b.1) were added while stirring vigorously. Then the mixture was heated to 50° C. In the course of this, complete dissolution of the D(+)-maltose (b.1) was achieved. After adding 9.6 ml of an 8 M solution of borane-pyridine complex in THF (76.9 mmol), the reaction mixture was stirred at 50° C. for 7 days. The reaction mixture was dialyzed for 4 days against double-distilled water, and the product obtained was freeze-dried. Inventive hyperbranched polymer (A3.1-1-2) was obtained as a white amorphous product with a yield of 21% (7.0 g).

II.5 Preparation of Inventive Hyperbranched Polymer (A2.1-1-2)

In a 1 l flask, 10 g of hyperbranched polyurea (a2.1), corresponding to 4.64 mmol of $NH_2$ groups, were dissolved in 50 ml of aqueous 0.1 M sodium borate buffer and the mixture was stirred at room temperature for one hour. Then 1.67 g (4.64 mmol) of D(+)-maltose (b.1) were added while stirring vigorously. Then the mixture was heated to 50° C. In the course of this, complete dissolution of the D(+)-maltose (b.1) was achieved. After adding 0.58 ml of an 8 M solution of borane-pyridine complex in THF (46.4 mmol), the reaction mixture was stirred at 50° C. for 7 days. The reaction mixture was dialyzed for 4 days against double-distilled water, and the product obtained was freeze-dried. Inventive hyperbranched polymer (A2.1-1-2) was obtained as a white amorphous product with a yield of 30% (3.5 g).

III. Solubilization Experiments—Procedure for Solubilization of Pyrene with Inventive Hyperbranched Polymer (A2.1-1-1)

100 mg of inventive hyperbranched polymer (A2.1-1-1) were weighed into a 50 ml beaker and dissolved in 9.9 g of distilled water. Subsequently, 100 mg of pyrene were weighed into the mixture in order to obtain an oversaturated solution. The mixture was then stirred at room temperature with the aid of a magnetic stirrer for 24 h. After a wait time of one hour, excess (i.e. unsolubilized) active ingredient was removed by centrifuging. The clear solution thus obtained was subsequently analyzed by means of UV spectroscopy for its active ingredient content. The wavelength of the UV spectroscopy measurement was 334 nm.

The results of the solubilization tests are compiled in table 1.

TABLE 1

Solubility of pyrene [mg/l] in water without and with hyperbranched polymer (A)

| Hyperbranched polymer | Pyrene |
|---|---|
| none | 0.1 |
| (A2.1-1-1) | 12.9 |

The invention claimed is:

1. A process for solubilizing a hydrophobic active ingredient in aqueous medium, which comprises using, as an assistant, at least one hyperbranched polymer (A) which is obtained by a process comprising reacting at least one hyperbranched polymeric compound having at least one primary or secondary amino group per molecule (a) with (b) at least one mono-, di- or oligosaccharide,
   wherein the at least one hyperbranched polymeric compound is selected from the group consisting of
   (a1) a hyperbranched polyamide and
   (a2) a hyperbranched as polyurea.

2. The process according to claim 1, wherein hyperbranched polymer (A) has a mean molecular weight Mw in the range from 1000 to 100 000 g/mol.

3. The process according to claim 1, wherein hydrophobic active ingredient is at least one selected from the group consisting of a crop protection agent and a pharmaceuticallly active substance.

4. The process according to claim 1, wherein hydrophobic active ingredient is at least one selected from the group consisting of an insecticide and a fungicide.

5. The process according to claim 1, wherein the oligosaccharide is selected from compounds formed from three to 20 monosaccharide units per molecule which may be the same or different.

6. The process according to claim 1, wherein the hyperbranched polyamide is a hyperbranched polylysine (a3).

7. A water-soluble or water-dispersible hyperbranched polymer (A), obtained by a process comprising reacting at least one hyperbranched polymeric compound having at least one primary or secondary amino group per molecule (a) with (b) at least one mono-, di- or oligosaccharide, wherein the at least one hyperbranched polymeric compound is selected from the group consisting of
- (a1) a hyperbranched polyamide and
- (a2) a hyperbranched polyurea.

8. A hyperbranched polymer (A) according to claim 7, wherein the oligosaccharide is selected from compounds formed from three to 20 monosaccharide units per molecule which may be the same or different.

9. A hyperbranched polymer (A) according to claim 7, which has a mean molecular weight Mw in the range from 1000 to 100 000 g/mol.

10. A hyperbranched polymer (A) according to claim 7, wherein the mono-, di- or oligosaccharide (b) is bonded glycosidically to the hyperbranched polymeric compound (a).

11. A hyperbranched polymer (A) according to claim 7, wherein the hyperbranched polyamide (a1) is a hyperbranched polylysine (a3).

12. A process for preparing hyperbranched polymers (A) according to claim 7, which comprises reacting at least one hyperbranched polymeric compound having at least one primary or secondary amino group per molecule (a) with (b) at least one mono-, di- or oligosaccharide in the liquid phase under reductive amination conditions, wherein the at least one hyperbranched polymeric compound is selected from the group consisting of
- (a1) a hyperbranched polyamide and
- (a2) a hyperbranched polyurea.

13. The process according to claim 12, wherein the reductive amination is performed with the aid of a borane-Lewis base complex.

14. The process according to claim 12, wherein the reductive amination is performed with the aid of a borane-pyridine complex.

15. A complex comprising at least one hyperbranched polymer (A) according to claim 7 and at least one hydrophobic active ingredient.

16. An aqueous formulation comprising at least one complex according to claim 15.

17. A process for preparing complexes according to claim 15, which comprises mixing at least one hyperbranched polymer (A) and at least one hydrophobic active ingredient with one another.

* * * * *